United States Patent
Perumalla et al.

(10) Patent No.: US 12,063,127 B2
(45) Date of Patent: Aug. 13, 2024

(54) SMART REFRIGERATOR FOR SMART CONSUMPTION OF FOOD

(71) Applicant: INTERNATIONAL BUSINESS MACHINES CORPORATION, Armonk, NY (US)

(72) Inventors: Saraswathi Sailaja Perumalla, Visakhapatnam (IN); Shanthan Chamala, Malverne, PA (US); Venkata Vara Prasad Karri, Visakhapatnam (IN); Sri Harsha Varada, Vizianagaram (IN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 802 days.

(21) Appl. No.: 17/248,945

(22) Filed: Feb. 15, 2021

(65) Prior Publication Data

US 2022/0263680 A1 Aug. 18, 2022

(51) Int. Cl.
*H04L 12/28* (2006.01)
*G06F 18/213* (2023.01)
*G06F 18/214* (2023.01)
*G16H 10/60* (2018.01)
*G16H 20/60* (2018.01)
*G16H 50/30* (2018.01)

(52) U.S. Cl.
CPC ........ *H04L 12/2829* (2013.01); *G06F 18/213* (2023.01); *G06F 18/214* (2023.01); *G16H 10/60* (2018.01); *G16H 20/60* (2018.01); *G16H 50/30* (2018.01); *H04L 2012/285* (2013.01)

(58) Field of Classification Search
CPC .......... H04L 12/2829; H04L 2012/285; G16H 10/60; G16H 50/30; G16H 20/60; G06F 18/214; G06F 18/213
See application file for complete search history.

(56) References Cited

U.S. PATENT DOCUMENTS

| | | | |
|---|---|---|---|
| 2013/0138656 A1 | 5/2013 | Wheaton | |
| 2017/0308666 A1* | 10/2017 | Thomson | ............... G16H 10/60 |
| 2018/0129998 A1 | 5/2018 | Frazier | |
| 2019/0034556 A1 | 1/2019 | Gu | |

(Continued)

FOREIGN PATENT DOCUMENTS

| | | |
|---|---|---|
| CN | 105117450 A | 12/2015 |
| CN | 109631486 A | 4/2019 |

OTHER PUBLICATIONS

Arthurs, "ThinQ Smart refrigerator: Talking Diet Fridge Keeps your weight in check", https://www.dailymail.co.uk/email/article-2084729/ThinQ-Smart-refrige . . . , Jan. 11, 2012, pp. 1-37.

(Continued)

*Primary Examiner* — Eddy Saint-Vil
(74) *Attorney, Agent, or Firm* — Rakesh Roy

(57) ABSTRACT

The exemplary embodiments disclose a method, a computer program product, and a computer system for managing a consumption of food. The exemplary embodiments may include collecting data of a user and of one or more food items, extracting one or more features from the collected data, and determining a food consumption recommendation based on the extracted one or more features and one or more models.

20 Claims, 8 Drawing Sheets

(56) References Cited

U.S. PATENT DOCUMENTS

2019/0228855 A1* 7/2019 Leifer .................... G16H 20/60
2019/0281878 A1* 9/2019 Tang ...................... G16H 20/60
2019/0295440 A1* 9/2019 Hadad .................... G16H 20/60
2019/0303709 A1* 10/2019 Hu ....................... G06F 18/2113

OTHER PUBLICATIONS

Balica, "Fighting Food Poverty with Neighborhood Fridges", https://popupcity.net/observations/fighting-food-poverty-with-neighborh . . . , Feb. 15, 2017, pp. 1-6.

Burger, "Study: A lot of food goes into the fridge to die", The Columbus Dispatch, https://www.dispatch.com/news/20190902/study-lot-of-food-goes-into-fr . . . , Sep. 2, 2019, pp. 1-3.

Cleanmetrics, "Food waste: Impact Analysis and reduction", https://www.cleanmetrics.com/html/food_waste_offerings.htm, accessed Jan. 25, 2021, pp. 1-2.

Farr_Wharton et al., "Colour Coding the Fridge to Reduce Food Waste", https://www.researchgate.net/publication/266653365_Colour_Coding_the_Fridge_to_Reduce_Food_Waste, Nov. 2012, pp. 1-7.

Jacobs, "This Communal Fridge is Pretty Damm Amazing", https://grist.org/food/this-communal-fridge-is-pretty-damn-amazing/, Aug. 13, 2015, pp. 1-3.

Johnson, "Coca-Cola experiments with smart fridges to bridge in-store, mobile engagement", https://www.marketingdive.com/ex/mobilemarketer/cms/news/software- . . . , accessed Jan. 25, 2020, pp. 1-4.

Khosta, "Most Refrigerated Foods Gets Thrown Out Even Before it Goes Bad, Says New Survey", NDTV Food, https://food.ndtv.com/news/most-refrigerated-food-gets-thrown-out-even-before-it-goes-bad-says-new-survey-2092474, Aug. 30, 2019, pp. 1-4.

Mell et al., "The NIST Definition of Cloud Computing", National Institute of Standards and Technology, Special Publication 800-145, Sep. 2011, pp. 1-7.

Rouillard, "The Pervasive Fridge. A Smart Computer System Against Uneaten Food Loss", https://hal.archives-ouvertes.fr/hal-00825886/document, May 24, 2013, pp. 1-7.

Samsung, "Samsung Empowers Life in the Kitchen with Family Hub Refrigerator", https://news.samsung.com/us/2017-samsung-family-hub-refrigerator-an . . . , Jun. 20, 2017, pp. 1-7.

Schanes et al., "Food Waste Matters—A systematic review of household food waste practices", https://www.sciencedirect.com/science/article/pii/S0959652618303366, Science Direct, Journal of Cleaner Production, vol. 182, May 2018, pp. 1-46.

Semel, "How Might we dramatically reduce waste by transforming our relationship with food?" Expire: The App that Reminds you when your food is about to go bad [update Oct. 15—Wesite Addition], https://challenges.openideo.com/challenge/food-waste/ideas/expire-the-a . . . , Oct. 15, 2016, pp. 1-19.

Takahashi, "Smarter's FridgeCam can guess when your food expires", https://venturebeat.com/2017/01/03/smarters-fridgecam-tells-you-whe- . . . , Jan. 3, 2017, pp. 1-6.

* cited by examiner

SMART REFRIGERATOR FOR SMART CONSUMPTION OF FOOD

BACKGROUND

The exemplary embodiments relate generally to a smart refrigerator (smart fridge), and more particularly to using a smart fridge for smart consumption of food.

Many people purchase a lot of items and groceries and store them in their refrigerator (fridge). Many people forget to keep track of expiration dates of those items and shelf lives of those groceries. This results in a lot of food wastage. For example, a busy person may forget that their items in their fridge are about to expire in two days. The person may wish to be notified that those items are going to expire in two days, so that they can plan to consume those items prior to expiration and avoid wasting the items.

SUMMARY

The exemplary embodiments disclose a method, a computer program product, and a computer system for managing a consumption of food. The exemplary embodiments may include collecting data of a user and of one or more food items, extracting one or more features from the collected data, and determining a food consumption recommendation based on the extracted one or more features and one or more models.

BRIEF DESCRIPTION OF THE SEVERAL VIEWS OF THE DRAWINGS

The following detailed description, given by way of example and not intended to limit the exemplary embodiments solely thereto, will best be appreciated in conjunction with the accompanying drawings, in which.

The drawings are not necessarily to scale. The drawings are merely schematic representations, not intended to portray specific parameters of the exemplary embodiments. The drawings are intended to depict only typical exemplary embodiments. In the drawings, like numbering represents like elements.

DETAILED DESCRIPTION OF THE SEVERAL VIEWS OF THE DRAWINGS

Figure 1:
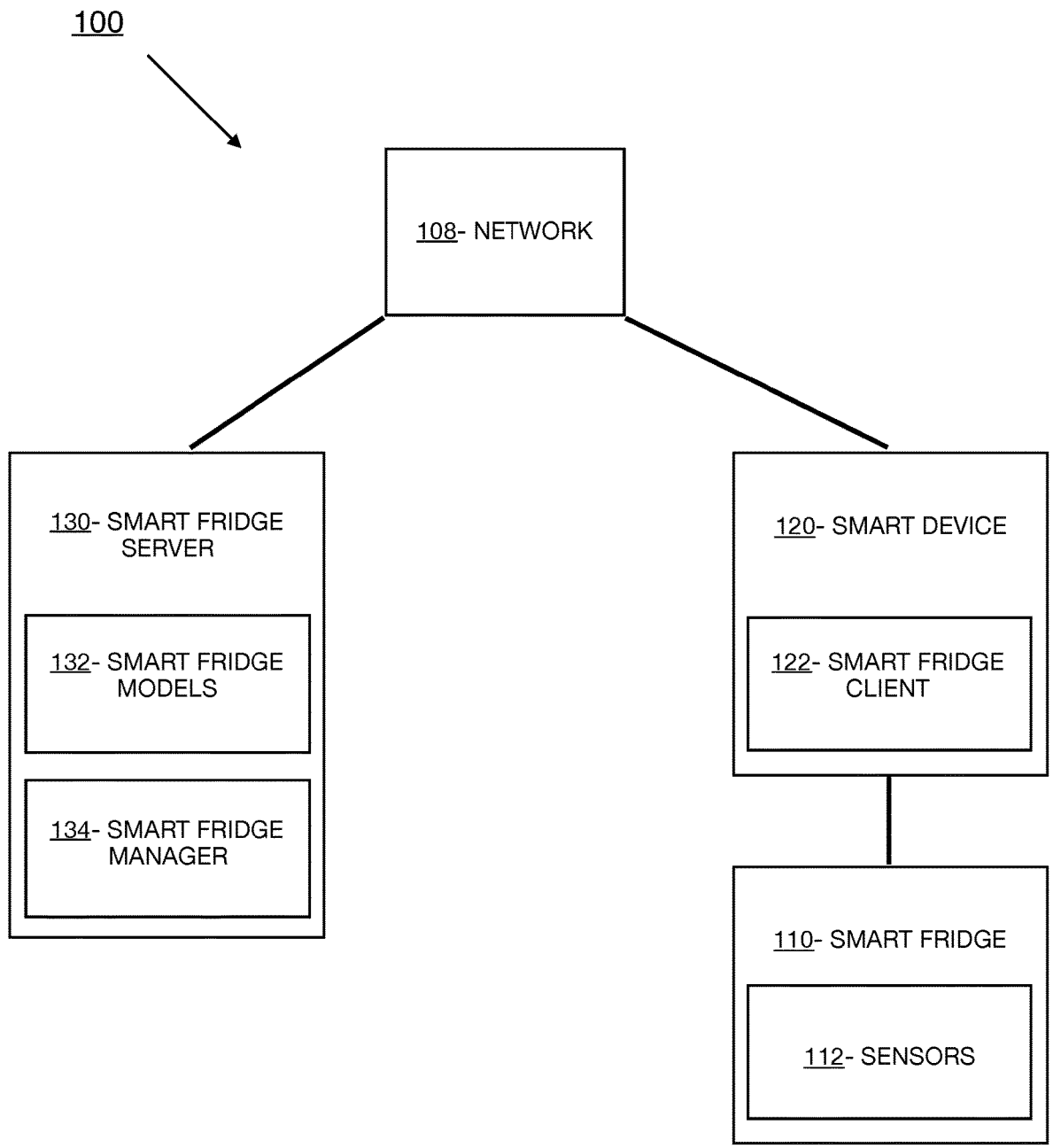
FIG. 1 depicts an exemplary schematic diagram of a smart fridge system 100, in accordance with the exemplary embodiments.

Detailed embodiments of the claimed structures and methods are disclosed herein; however, it can be understood that the disclosed embodiments are merely illustrative of the claimed structures and methods that may be embodied in various forms. The exemplary embodiments are only illustrative and may, however, be embodied in many different forms and should not be construed as limited to the exemplary embodiments set forth herein. Rather, these exemplary embodiments are provided so that this disclosure will be thorough and complete, and will fully convey the scope to be covered by the exemplary embodiments to those skilled in the art. In the description, details of well-known features and techniques may be omitted to avoid unnecessarily obscuring the presented embodiments.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to implement such feature, structure, or characteristic in connection with other embodiments whether or not explicitly described.

In the interest of not obscuring the presentation of the exemplary embodiments, in the following detailed description, some processing steps or operations that are known in the art may have been combined together for presentation and for illustration purposes and in some instances may have not been described in detail. In other instances, some processing steps or operations that are known in the art may not be described at all. It should be understood that the following description is focused on the distinctive features or elements according to the various exemplary embodiments.

Many people purchase a lot of items and groceries and store them in their refrigerator (fridge). Many people forget to keep track of expiration dates of those items and shelf lives of those groceries. This results in a lot of food wastage. For example, a busy person may forget that their items in their fridge are about to expire in two days. The person may wish to be notified that those items are going to expire in two days, so that they can plan to consume those items prior to expiration and avoid wasting the items.

Exemplary embodiments are directed to a method, computer program product, and computer system for managing the consumption of food. In embodiments, machine learning may be used to create models capable of determining one or more food consumption recommendations to a user, while feedback loops may improve upon such models. Moreover, data from user uploads, databases, network 108, or the sensors 112 may be used to determine one or more food consumption recommendations to a user.

Many users may wish for their fridge to keep track of items' shelf lives, expiration dates, compatibility for recipes, etc. in order to reduce food wastage and make food consumption recommendations. In embodiments, food consumption recommendations may pertain to best times to consume food, best recipes to use to consume food, best times to donate food that will not be consumed, etc. For example, a person may anticipate traveling for two weeks on vacation and may be cleaning out the items in their fridge that may expire over those two weeks. The person may wish for their fridge to assist them in identifying items that can be kept until they return two weeks later as well as items that could be donated prior to the two-week vacation. In another example, a commercial chef at a restaurant may wish to know recipes that would use food items that are near expiration, such that the food items will not ultimately be wasted. In general, it will be appreciated that embodiments described herein may relate to aiding in the consumption of food within any environment and for any motivation.

FIG. 1 depicts the smart fridge system 100, in accordance with the exemplary embodiments. According to the exemplary embodiments, the smart fridge system 100 may include a smart fridge 110, a smart device 120, and a smart fridge server 130, which may all be interconnected via a network 108. In embodiments, the smart fridge system 100 may include additional elements such as multiple smart fridges, one or more smart rangers or smart stoves, etc. While programming and data of the exemplary embodiments may be stored and accessed remotely across several servers via the network 108, programming and data of the exemplary embodiments may alternatively or additionally be stored locally on as few as one physical computing device or amongst other computing devices than those depicted.

In the exemplary embodiments, the network 108 may be a communication channel capable of transferring data between connected devices. Accordingly, the components of the smart fridge system 100 may represent network components or network devices interconnected via the network 108. In the exemplary embodiments, the network 108 may be the Internet, representing a worldwide collection of networks and gateways to support communications between devices connected to the Internet. Moreover, the network 108 may utilize various types of connections such as wired, wireless, fiber optic, etc. which may be implemented as an intranet network, a local area network (LAN), a wide area network (WAN), or a combination thereof. In further embodiments, the network 108 may be a Bluetooth network, a Wi-Fi network, or a combination thereof. In yet further embodiments, the network 108 may be a telecommunications network used to facilitate telephone calls between two or more parties comprising a landline network, a wireless network, a closed network, a satellite network, or a combination thereof. In general, the network 108 may represent any combination of connections and protocols that will support communications between connected devices.

In the exemplary embodiments, the smart fridge 110 may include one or more sensors 112 and may be one or more smart refrigerator, enterprise server, laptop computer, notebook, tablet computer, netbook computer, personal computer (PC), desktop computer, server, personal digital assistant (PDA), rotary phone, touchtone phone, smart phone, mobile phone, virtual device, thin client, virtual reality device, augmented reality device, or any other electronic device or computing system capable of receiving and sending data to and from other computing devices. While each smart fridge 110 is shown as a single device, in other embodiments, each smart fridge 110 may be comprised of a cluster or plurality of computing devices, in a modular manner, etc., working together or working independently. The smart fridge may for example comprise multiple bins or sections for various types of food (humidity-controlled crisper bin, temperature-controlled defroster bin, etc.) each with one or more sensors 112. The smart fridge 110 may additionally comprise one or more mechanisms to move food items from one bin to another, or to eject a food item outside the smart fridge 110. For example, the smart fridge 110 may comprise one or more mechanical arms (i.e., actuators functioning together) that allow for food items to be picked up and placed elsewhere, for bins to be opened and closed, etc. The smart fridge 110 is described in greater detail as a hardware implementation with reference to FIG. 6, as part of a cloud implementation with reference to FIG. 7, and/or as utilizing functional abstraction layers for processing with reference to FIG. 8.

In example embodiments, the sensors 112 may comprise a camera, microphone, light sensor, infrared sensor, movement detection sensor, pressure sensor, humidity sensor, thermometer, global positioning system (GPS) sensor, or other sensory hardware equipment. Moreover, the smart fridge 110 may incorporate an array of the one or more sensors 112 such that information can be obtained by the sensors 112 in multiple directions, at different times/intervals, in different mediums/frequencies, and the like. For example, the smart fridge 110 may include three inward-facing cameras located on the inside of the smart fridge 110 door that each record an adjacent sixty-degree viewing angle spanning a total of one-hundred and eighty degrees into the fridge. Moreover, data processing techniques may be implemented such that directional information of visual and audio data can be obtained based on signals received by each of the three sensors 112, such as trilateration and triangulation. In another example, the smart fridge 110 may include a camera, thermometer, and humidity sensors in each bin or compartment of the smart fridge 110.

While the sensors 112 are depicted as integrated with the smart fridge 110, in embodiments, the sensors 112 may be incorporated within an environment in which the smart fridge system 100 is implemented. For example, the sensors 112 may be one or more thermometers built into a kitchen or living room, a camera built into a facility, etc. Moreover, data processing techniques may be implemented such that directional information of visual and audio data can be obtained based on signals received by each of the sensors 112, such as trilateration and triangulation. In other embodiments, the sensors 112 may be integrated with other smart devices, e.g., smart phones and laptops, within an environment implementing the smart fridge system 100. In such embodiments, the sensors 112 may communicate directly with other networks and devices, such as the network 108. The sensors 112 are described in greater detail as a hardware implementation with reference to FIG. 6, as part of a cloud implementation with reference to FIG. 7, and/or as utilizing functional abstraction layers for processing with reference to FIG. 8.

In the example embodiment, the smart device 120 includes a smart fridge client 122, and may be an enterprise server, a laptop computer, a notebook, a tablet computer, a netbook computer, a personal computer (PC), a desktop computer, a server, a personal digital assistant (PDA), a rotary phone, a touchtone phone, a smart phone, a mobile phone, a virtual device, a thin client, an IoT device, or any other electronic device or computing system capable of receiving and sending data to and from other computing devices. While the smart device 120 is shown as a single device, in other embodiments, the smart device 120 may be comprised of a cluster or plurality of computing devices, in a modular manner, etc., working together or working independently. The smart device 120 is described in greater detail as a hardware implementation with reference to FIG.

Figure 7:
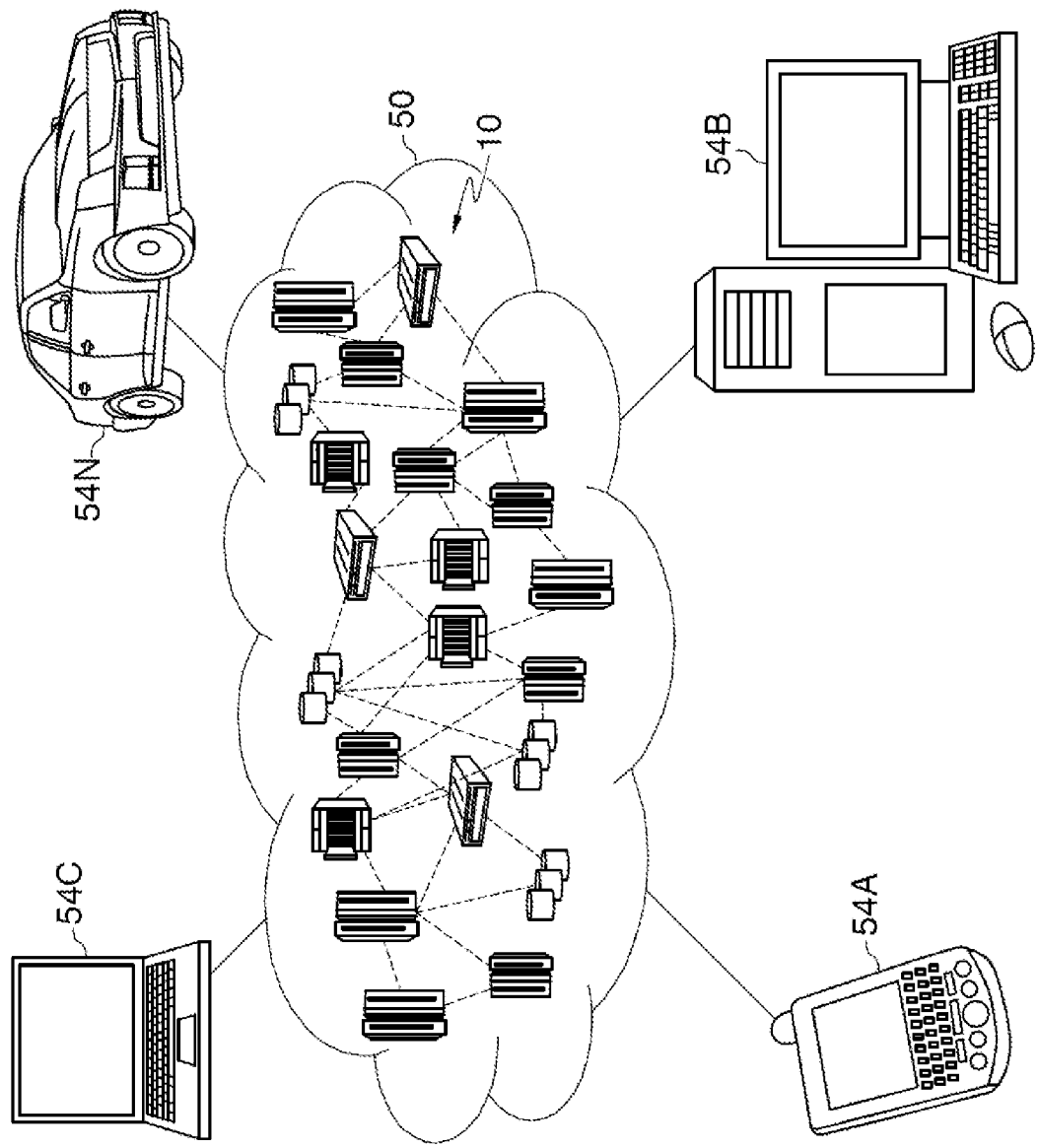
FIG. 7 depicts a cloud computing environment, in accordance with the exemplary embodiments.
Figure 8:
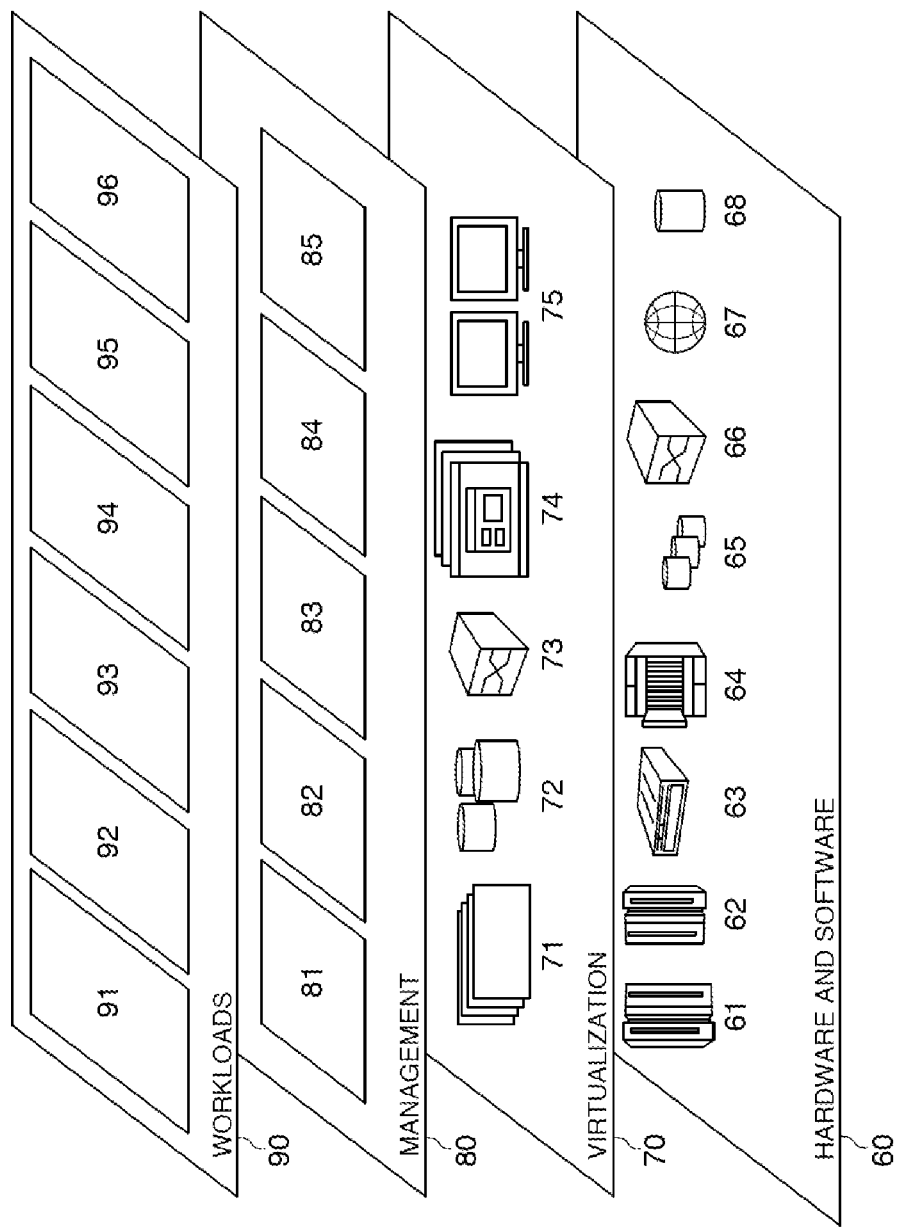
FIG. 8 depicts abstraction model layers, in accordance with the exemplary embodiments.

6, as part of a cloud implementation with reference to FIG. 7, and/or as utilizing functional abstraction layers for processing with reference to FIG. 8.

The smart fridge client 122 may act as a client in a client-server relationship. The smart fridge client 122 may also be a software and/or hardware application capable of communicating with and providing a user interface for a user to interact with a server, for example the smart fridge server 130, via the network 108. Moreover, in the example embodiment, the smart fridge client 122 may be capable of transferring data from the smart fridge 110 and/or the sensors 112 between the smart device 120 and other devices via the network 108. In embodiments, the smart fridge client 122 utilizes various wired and wireless connection protocols for data transmission and exchange, including Bluetooth, 2.4 gHz and 5 gHz internet, near-field communication, Z-Wave, Zigbee, etc. The smart fridge client 122 is described in greater detail with respect to FIG. 2.

In the exemplary embodiments, the smart fridge server 130 may include one or more smart fridge models 132 and a smart fridge manager 134 and may act as a server in a client-server relationship with the smart fridge client 122. The smart fridge server 130 may be an enterprise server, a laptop computer, a notebook, a tablet computer, a netbook computer, a PC, a desktop computer, a server, a PDA, a rotary phone, a touchtone phone, a smart phone, a mobile phone, a virtual device, a thin client, an IoT device, or any other electronic device or computing system capable of receiving and sending data to and from other computing devices. While the smart fridge server 130 is shown as a single device, in other embodiments, the smart fridge server 130 may be comprised of a cluster or plurality of computing devices, working together or working independently. The smart fridge server 130 is described in greater detail as a hardware implementation with reference to FIG. 6, as part of a cloud implementation with reference to FIG. 7, and/or as utilizing functional abstraction layers for processing with reference to FIG. 8.

The smart fridge models 132 may be one or more algorithms modelling a correlation between one or more features detected by the sensors 112 and one or more food consumption recommendations. In the example embodiment, the smart fridge models 132 may be generated using machine learning methods, such as neural networks, deep learning, hierarchical learning, Gaussian Mixture modelling, Hidden Markov modelling, and K-Means, K-Medoids, or Fuzzy C-Means learning, etc., and may model a likelihood of the one or more features being indicative of an accurate or appropriate food consumption recommendation. In embodiments, such features may pertain to items in a smart fridge 110 and may include type, date purchased, expiration date, shelf life, quantity, temperature, humidity, possible recipes, recipe preparation times, healthiness, etc. In embodiments, such features may additionally pertain to one or more users and may include calendars, medical information, allergy information, dietary restrictions, dietary preferences, etc. The smart fridge models 132 may weight the features based on an effect that the features have on making an appropriate food consumption recommendation. The smart fridge models 132 are described in greater detail with reference to FIG. 2.

In the exemplary embodiments, the smart fridge manager 134 may be a software and/or hardware program capable of collecting training data, extracting features from the training data, and training one or more models based on the extracted features. The smart fridge manager 134 may additionally be capable of configuring a session and collecting data. The smart fridge manager 134 may further extract features from the collected data and apply one or more models to the extracted features to make one or more food consumption recommendations. Moreover, the smart fridge manager 134 may be further configured for notifying a user of the one or more food consumption recommendations, evaluating whether the one or more recommendations were appropriate, adjusting the one or more models, and facilitating one or more actions based on the one or more recommendations. The smart fridge manager 134 is described in greater detail with reference to FIG. 2.

Figure 2:
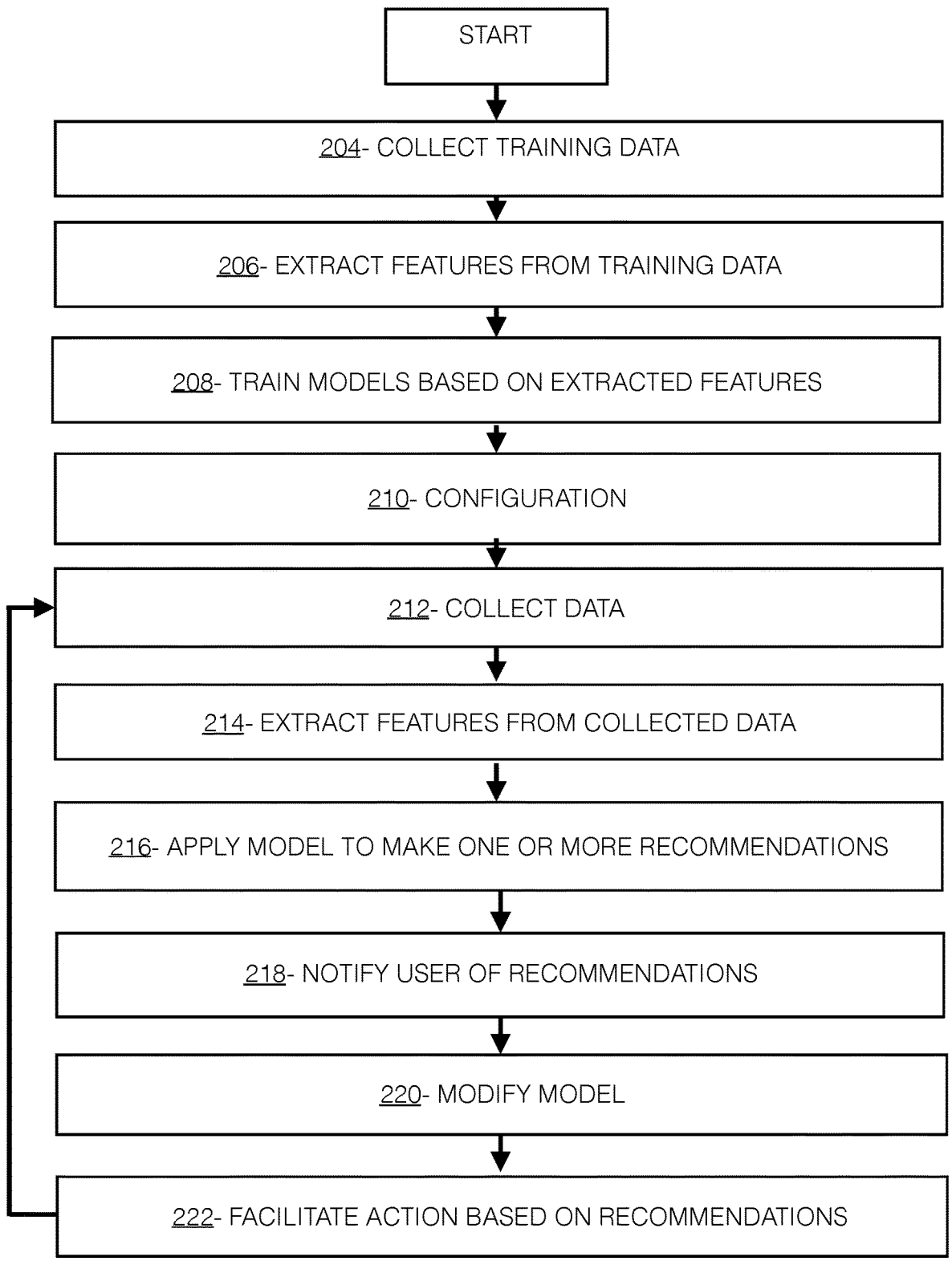
FIG. 2 depicts an exemplary flowchart illustrating the operations of a smart fridge manager 134 of the smart fridge system 100 in managing the consumption of food, in accordance with the exemplary embodiments.

FIG. 2 depicts an exemplary flowchart illustrating the operations of a smart fridge manager 134 of the smart fridge system 100 in managing the consumption of food, in accordance with the exemplary embodiments. In exemplary embodiments, the smart fridge manager 134 first implements a training phase in which it trains the smart fridge models 132 using labelled training data from previous interactions between one or more users and one or more smart fridges 110. The smart fridge manager 134 then moves on to an operational phase in which it applies the trained smart fridge models 132 to current data in order to make one or more appropriate food consumption recommendations.

The smart fridge manager 134 may collect and/or receive training data (step 204). In embodiments, the training data may be sourced from previous interactions between one or more users and one or more smart fridges 110. Training data may include data of one or more user's calendars, medical records, allergy records, dietary restrictions, dietary preferences, locations, number of guests, guests' dietary restrictions, dietary preferences, and audio and video data of the user's smart fridge 110 labelled with one or more food consumption recommendations. For example, training data may include data of a user's allergy to apples and video footage of an apple in the user's smart fridge 110 labelled with recommendation, "Reminder: you are allergic to apples." In a second example, training data may include footage of various food items placed in a smart fridge 110 at various times labelled with recommendation, "Left over pizza will spoil in two days. Perhaps eat pizza for dinner tonight. The bread will soon not be fresh. Perhaps eat the bread with peanut butter as a sandwich for lunch today." In a third example, training data may include footage of various food items placed in a smart fridge 110 at various times along with a user's calendar labelled with recommendation, "It does not appear you will be able to consume the unopened jam and canned beans before their expiration. Perhaps you should donate these items at 10 am tomorrow. Your calendar shows you are available at this time." The smart fridge manager 134 may collect training data from microphones and video cameras, which may be built into the user's smart fridge 110. The smart fridge manager 134 may retrieve training data via user upload, databases, or the sensors 112. In embodiments, the smart fridge manager 134 may collect training data via the sensors 112 as one or more microphones built into a kitchen, a camera built into a smart fridge 110 door, etc. The collected training data may pertain to items in a smart fridge 110 and may relate to the type, date purchased, expiration date, shelf life, quantity, temperature, humidity, possible recipes, recipe preparation times, healthiness, etc. of those items. The collected training data may additionally pertain to one or more users and may relate to calendars, medical information, allergy information, dietary restrictions, dietary preferences, etc.

In embodiments, the smart fridge manager 134 may collect and/or receive training data of one or more appropriate syntaxes for training purposes. For example, training data may include template sentences such as "[Item] will expire on [day]," "Perhaps you should eat [recipe] for [breakfast/lunch/dinner] on [day]" and "It does not appear that you will be able to consume [item] before it expires on [day]. Perhaps you should donate [item] on [day] since your calendar shows you are available." The smart fridge manager 134 may mirror the syntax of received template sentences when later making one or more food consumption recommendations.

To further illustrate the operations of the smart fridge manager 134, reference is now made to an illustrative example where the smart fridge manager 134 collects labelled training data of previous interactions between one or more users and one or more smart fridges 110. For each user interaction, the smart fridge manager 134 collects data of the contents of a user's smart fridge 110 and user data from one or more databases labelled with the smart fridge 110's appropriate food consumption recommendation to the user. The smart fridge manager 134 additionally collects template sentences for syntax purposes.

The smart fridge manager 134 may extract one or more features from the collected and/or received training data (step 206). The extracted features may be extracted from the audio, video, etc. data and/or databases, and may include features pertaining to items in a smart fridge 110 such as type, date purchased, expiration date, shelf life, quantity, temperature, humidity, possible recipes, recipe preparation times, healthiness, etc. In embodiments, such features may additionally pertain to one or more users and may include calendars, medical information, allergy information, dietary restrictions, dietary preferences, etc. In embodiments, the smart fridge manager 134 may use techniques such as feature extraction, natural language processing, named entity recognition, optical character recognition, image processing, video processing, audio processing, pattern/template matching, data comparison, convolutional neural networks, etc. to identify features. For example, the smart fridge manager 134 may extract features such as calendars, medical information, allergy information, dietary restrictions, dietary preferences, etc. directly from one or more databases using feature extraction and optical character recognition. The smart fridge manager 134 may extract features such as shelf life, possible recipes, recipe preparation times, healthiness, etc. directly from the internet via network 108 using image processing, pattern/template matching, data comparison, etc. The smart fridge manager 134 may additionally extract temperature and humidity directly from thermometers and humidity sensors as the sensors 112 using feature extraction. The smart fridge manager 134 may also extract item types, dates purchased, expiration dates, etc. from collected video and audio footage of one or more sensors 112 (i.e. user placing item in smart fridge 110 or footage of food labels stating expiration dates) using audio processing, video processing, etc. The smart fridge manager 134 may later associate extracted features with the labelled appropriate food consumption recommendations.

With reference to the previously introduced example where the smart fridge manager 134 collects labelled training data of previous interactions between one or more users and one or more smart fridges 110, the smart fridge manager 134 extracts features of each item in smart fridges 110 such as type, date purchased, expiration date, shelf life, quantity, temperature, humidity, possible recipes, recipe preparation times, healthiness, etc. as well as features of one or more users such as calendars, medical information, allergy information, dietary restrictions, dietary preferences, etc. from the collected training data with respect to previously received user interactions.

The smart fridge manager 134 may train one or more smart fridge models 132 based on the extracted features (step 208). The smart fridge manager 134 may train one or more smart fridge models 132 based on an association of the one or more extracted features with one or more food consumption recommendations. As previously mentioned, such extracted features may include features pertaining to items in a smart fridge 110 such as type, date purchased, expiration date, shelf life, quantity, temperature, humidity, possible recipes, recipe preparation times, healthiness, etc. In embodiments, such features may additionally pertain to one or more users and may include calendars, medical information, allergy information, dietary restrictions, dietary preferences, etc. The one or more smart fridge models 132 may be generated through machine learning techniques such as neural networks, and the smart fridge manager 134 may train the one or more smart fridge models 132 to weight the features such that features shown to have a greater correlation with making an appropriate food consumption recommendation are weighted greater than those features that are not. In embodiments, the smart fridge models 132 may include a model for each user. In other embodiments, the smart fridge manager 134 may simply train one smart fridge model 132 to be later applied to all users. Based on the smart fridge models 132's extracted features and weights associated with such extracted features, the smart fridge manager 134 may later determine one or more appropriate food consumption recommendations.

With reference to the previously introduced example where the smart fridge manager 134 extracts features from the collected training data with respect to previously received user interactions, the smart fridge manager 134 trains a model for each user of the collected training data.

The smart fridge manager 134 may receive a configuration (step 210). Having trained the one or more smart fridge models 132, the smart fridge manager 134 may now apply the one or more smart fridge models 132 to make one or more food consumption recommendations in real time. The smart fridge manager 134 may first, however, receive a user configuration by receiving a user registration and user preferences. The user registration may be uploaded by a user, i.e., a person using the smart fridge 110 of the smart fridge system 100 or administrator, i.e., a person overseeing the user's usage of the smart fridge system 100 (such as a parent or guardian of the user, employer of the user, etc.) and the configuration may be received by the smart fridge manager 134 via the smart fridge client 122 and the network 108. Receiving the user registration may involve referencing a user profile via user login credentials, internet protocol (IP) address, media access control (MAC) address, etc., or receiving user input information such as a name, date of birth, gender, address/geographic information, phone number, email address, company name, device serial numbers, one or more smart device 120 types, smart fridge 110 type, sensors 112 types, and the like. Receiving a user registration may also involve receiving or extracting data from databases such as user calendar data, social media data, health data, medical records, etc. Lastly, the smart fridge manager 134 may receive a configuration of the one or more sensors 112, whether they be fixed to one or more devices (e.g., the smart device 120 or the smart fridge 110) or fixed within an environment in which the smart fridge system 100 is implemented (e.g., fixed to a stove or fixed to the corner of a kitchen).

During configuration, the smart fridge manager 134 may further receive user preferences (step 210 continued). User preferences may include preferences for the timing or frequency of notification to the user of one or more recommendations. For example, user preferences may specify that the smart fridge manager 134 is to notify a user of expiring items only one day before their expiration. A different user may specify that the smart fridge manager 134 is to notify them of expiring items two days before their expiration. User preferences may additionally include preferences for the frequency of notification. For example, user preferences may specify that a user be notified on their smart device 120 and their smart fridge 110 once each day of any recommendations, whereas a different user may specify notification only on their smart device 120 but twice each day. User preferences may also specify when the smart fridge manager 134 should facilitate one or more actions based on the one or more recommendations. For example, user preferences may specify that user confirmation is required before events are created in a user's calendar for donating food items. A different user may specify that the smart fridge manager 134 is to schedule donations of food items in their calendar without seeking confirmation from the user.

With reference to the previously introduced example where the smart fridge manager 134 trains a model for each user of the collected training data, the smart fridge manager 134 receives a user registration via user upload including the user's name, type of smart device 120, type of smart fridge 110, types of sensors 112 including a microphone, video camera, thermometer, and humidity sensor, and links to databases containing user calendar data, medical data, allergy data, dietary restrictions, and dietary preferences. The smart fridge manager 134 also receives user preferences via user upload specifying that the user is to be notified of food consumption recommendations once daily via visual feedback on their smart device 120. The user preferences also specify that the smart fridge manager 134 must receive confirmation from the user prior to facilitating any actions based on the food consumption recommendations.

The smart fridge manager 134 may collect data (step 212). In embodiments, the smart fridge manager 134 may collect data of the user such as user calendar data, social media data, health data, medical data, allergy information, dietary restrictions, dietary preferences, etc. from one or more databases uploaded during configuration. In embodiments, the smart fridge manager 134 may additionally collect data of one or more items in the smart fridge 110 such as type, date purchased, expiration date, shelf life, quantity, temperature, humidity, possible recipes, recipe preparation times, healthiness, etc. from one or more sensors 112, which may include one or more microphones or video cameras built into the smart fridge 110, built into a kitchen, etc. In embodiments, the smart fridge manager 134 may continuously collect data from sensors 112 in anticipation of a user opening a door of the smart fridge 110. In embodiments, the smart fridge manager 134 may begin collecting data from sensors 112 upon one or more trigger, for example a user opening a smart fridge 110 door, opening a smart fridge 110 drawer or compartment, etc. The collected data may relate to data of items in a smart fridge 110 such as type, date purchased, expiration date, shelf life, quantity, temperature, humidity, possible recipes, recipe preparation times, healthiness, etc. In embodiments, collected data may additionally relate to one or more users and may include calendars, medical information, allergy information, dietary restrictions, dietary preferences, etc.

With reference to the previously introduced example where the smart fridge manager 134 receives a user registration and user preferences, the smart fridge manager 134 collects calendar, medical, allergy, and dietary data of the user from the databases uploaded during configuration. The smart fridge manager 134 additionally collects data of each item in the user's smart fridge 110 from the video camera, thermometer, and humidity sensor inside the smart fridge 110.

The smart fridge manager 134 may extract one or more features from the collected and/or received data (step 214). The smart fridge manager 134 may extract one or more features from the collected and/or received data in the same manner as described with reference to step 206, however here the features are extracted not from the training data, but rather from the currently collected data.

With reference to the previously introduced example where the smart fridge manager 134 collects data of the user and the items in the user's smart fridge 110, the smart fridge manager 134 extracts the below item features in Table 1 and user features in Table 2 from the collected data.

TABLE 1

| Extracted Item Features | |
| --- | --- |
| leftover pizza | date purchased: Jan. 22, 2021<br>expiration date: Jan. 28, 2021<br>quantity: four slices (2 servings)<br>temperature: 35 degrees Fahrenheit<br>humidity: 65%<br>healthiness: not healthy |
| salad | date purchased: Jan. 24, 2021<br>expiration date: Feb. 5, 2021<br>quantity: 3 servings<br>temperature: 35 degrees Fahrenheit<br>humidity: 65%<br>healthiness: very healthy |
| chicken | date purchased: Jan. 24, 2021<br>expiration date: Jan. 30, 2021<br>quantity: 2 servings<br>temperature: 35 degrees Fahrenheit<br>humidity: 65%<br>healthiness: healthy |
| apple | date purchased: Jan. 24, 2021<br>expiration date: Feb. 5, 2021<br>quantity: 4 apples (4 servings)<br>temperature: 35 degrees Fahrenheit<br>humidity: 30% (in crisper drawer)<br>healthiness: very healthy |

TABLE 2

| Extracted User Features | |
| --- | --- |
| calendar | availability Jan. 25, 2021 |
| medical records | diabetes, high cholesterol |
| allergy records | allergic to peanut butter |
| dietary restrictions | lactose intolerant |

Figure 3:
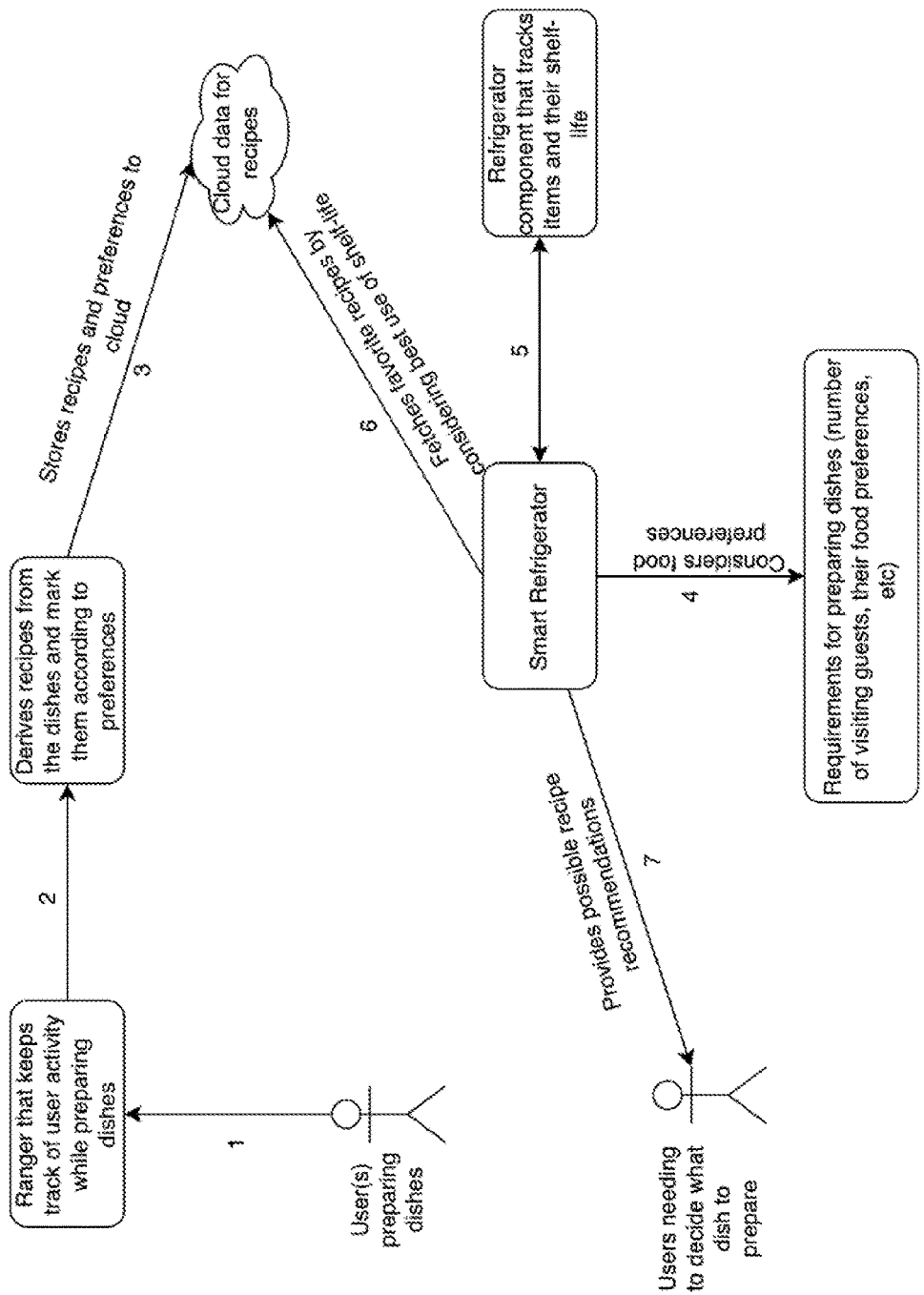
FIG. 3 depicts an exemplary flowchart illustrating the operations of a smart fridge manager 134 of the smart fridge system 100 in determining one or more preferred recipes of a user and recommending one or more recipes to the user, in accordance with the exemplary embodiments.
Figure 4:
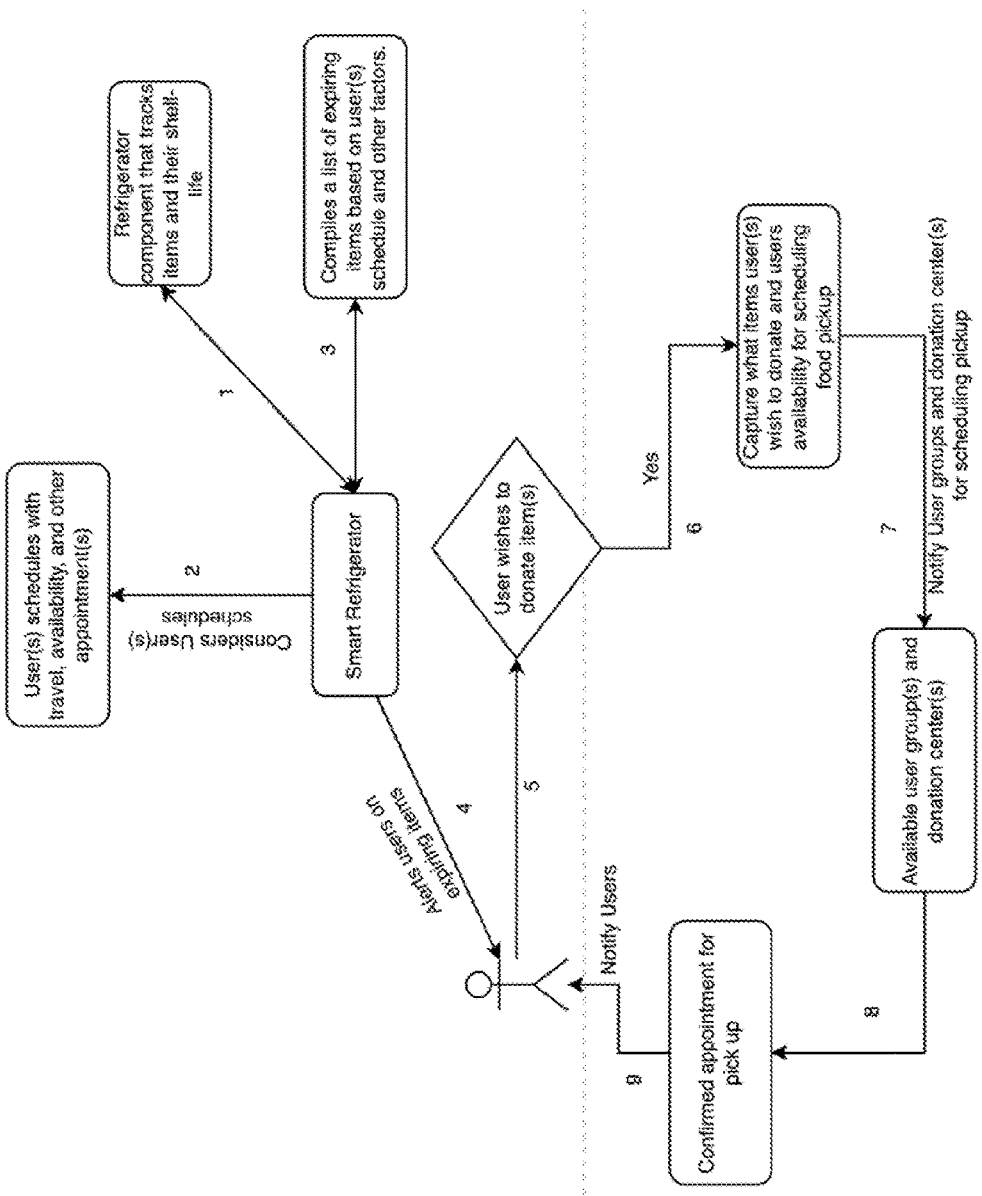
FIG. 4 depicts an exemplary flowchart illustrating the operations of a smart fridge manager 134 of the smart fridge system 100 in scheduling the giving away of food, in accordance with the exemplary embodiments.
Figure 5:
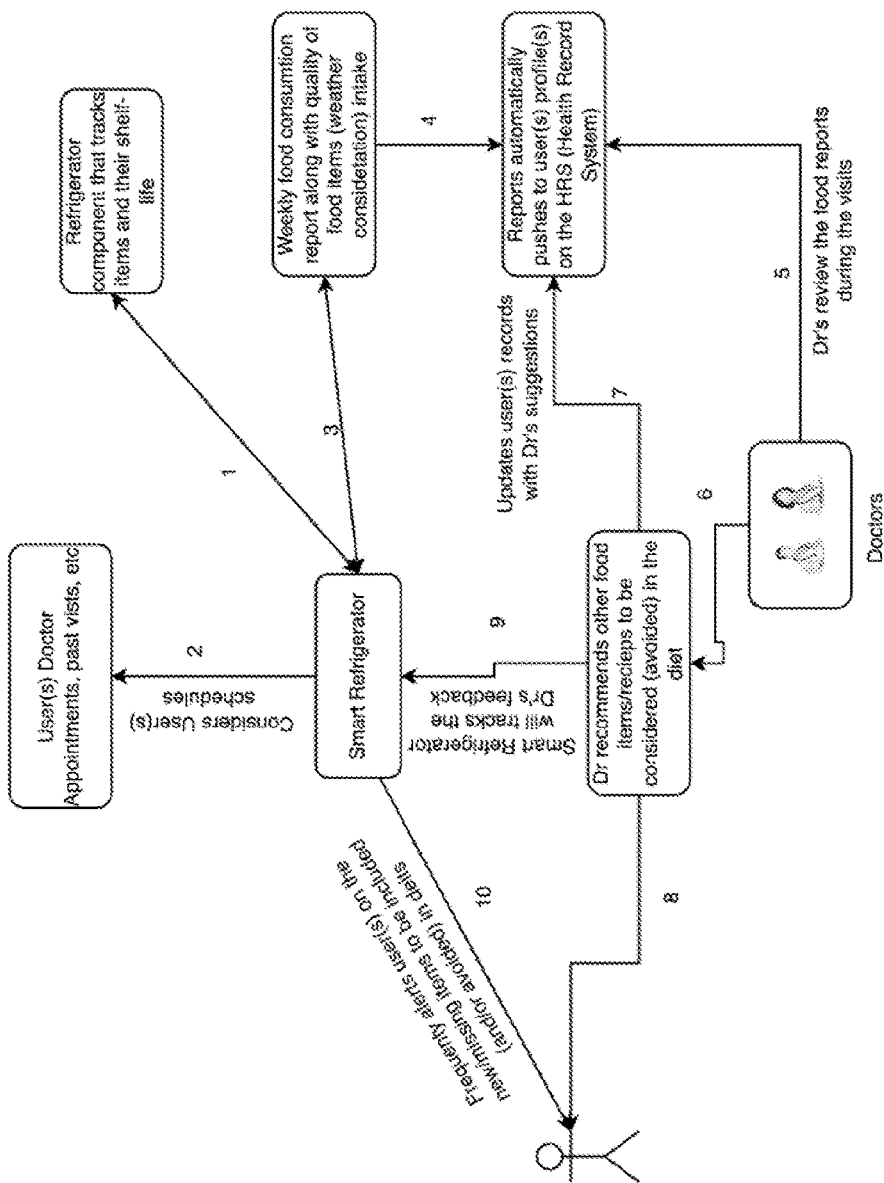
FIG. 5 depicts an exemplary flowchart illustrating the operations of a smart fridge manager 134 of the smart fridge system 100 in consulting one or more doctors for feedback and making recommendations to a user based on the feedback from the one or more doctors, in accordance with the exemplary embodiments.

The smart fridge manager 134 may apply one or more models to the extracted features to determine one or more food consumption recommendations (step 216). As previously mentioned, such extracted features may relate to items in a smart fridge 110 such as type, date purchased, expiration date, shelf life, quantity, temperature, humidity, possible recipes, recipe preparation times, healthiness, etc. In embodiments, features may additionally relate to one or more users and may include calendars, medical information, allergy information, dietary restrictions, dietary preferences, etc. and the one or more smart fridge models 132 may be generated through machine learning techniques such as neural networks. In embodiments, the one or more smart fridge models 132 may be trained at initialization and/or through the use of a feedback loop to weight the features such that features shown to have a greater correlation with determining an appropriate food consumption recommendation are weighted greater than those features that are not. Based on the extracted features and weights associated with such extracted features, the smart fridge manager 134 may determine one or more food consumption recommendations such as "Avoid eating [item] as it is bad for your health," "Consider donating [item] because you may not be able to consume prior to its expiration," "Consider combining [item] with [item] for a tasty meal," etc. With reference to FIG. 3-5, applying one or more models to the extracted features may determine food consumption recommendations pertaining to recipe suggestions, scheduling food donations, and medical recommendations.

With reference to the previously introduced example where the smart fridge manager 134 extracts features from the collected data, the smart fridge manager 134 applies the previously trained model for the user to determine the following appropriate food consumption recommendations: "The leftover pizza is expiring soon and is bad for your health conditions. Perhaps consider donating it during your availability on Jan. 25, 2021 prior to its expiration. Consider combining an apple, chicken, and salad for a tasty and healthy meal that is beneficial for your medical conditions."

Upon determining one or more appropriate food consumption recommendations, the smart fridge manager 134 may notify one or more users of the one or more food consumption recommendations (step 218). In embodiments, the smart fridge manager 134 may notify the user and/or the administrator of the determined recommendations. The smart fridge manager 134 may convey the one or more recommendations to the user and/or administrator in the form of audio, video, text, or any other manner via the smart device 120 and/or the smart fridge 110. In embodiments, the smart fridge manager 134 may notify the user and/or administrator of multiple food consumption recommendations at once. In other embodiments, the smart fridge manager 134 may notify the user and/or administrator of one recommendation at a time in a queue, and the smart fridge manager 134 may await feedback from the user and/or administrator indicative of whether one or more of the recommendations are appropriate. As discussed with reference to configuration, the smart fridge manager 134 may notify the user and/or administrator of one or more recommendations according to the user preferences of configuration. In embodiments, the smart fridge manager 134 may be configured for receiving user and/or administrator input acknowledging, dismissing, and/or affirming that one or more recommendations are appropriate and/or that one or more actions should be facilitated based on the one or more recommendations. With reference to FIG. 3-5, one or more users may be notified of food consumption recommendations pertaining to recipe suggestions, scheduling food donations, and medical recommendations.

With reference to the previously introduced example where the smart fridge manager 134 recommends, "The leftover pizza is expiring soon and is bad for your health conditions. Perhaps consider donating it during your availability on Jan. 25, 2021 prior to its expiration. Consider combining an apple, chicken, and salad for a tasty and healthy meal that is beneficial for your medical conditions," the smart fridge manager 134 notifies the user of the recommendations on their smart device via visual feedback according to the user preferences.

The smart fridge manager 134 may evaluate and modify the smart fridge models 132 (step 220). In the example embodiment, the smart fridge manager 134 may verify whether the one or more recommendations were appropriate and/or helpful in order to provide a feedback loop for modifying the smart fridge models 132. In embodiments, the feedback loop may simply provide a means for the user and/or administrator to indicate whether the one or more food consumption recommendations were appropriate and/or helpful to the user. The feedback loop indication may be triggered via a toggle switch, button, slider, etc. that may be selected by the user and/or administrator manually by hand using a button/touchscreen/etc., by voice, and the like. Based on the smart fridge manager 134 appropriately or inappropriately making one or more food consumption recommendations, the smart fridge manager 134 may modify the smart fridge models 132. In other embodiments, the smart fridge manager 134 may infer or deduce whether the recommendation was helpful to the user. For example, the smart fridge manager 134 may interpret user dialogue via natural language processing to determine whether the reply was helpful to the user. For example, if the user says, "No way! That doesn't help at all" or other expressions indicative of a user's dissatisfaction, the smart fridge manager 134 may infer that the recommendation was inappropriate and modify the smart fridge models 132 accordingly. Based on feedback received in the above or any other manners, the smart fridge manager 134 may then modify the smart fridge models 132 to more accurately make food consumption recommendations.

With reference to the previously introduced example where the smart fridge manager 134 notifies the user: "The leftover pizza is expiring soon and is bad for your health conditions. Perhaps consider donating it during your availability on Jan. 25, 2021 prior to its expiration. Consider combining an apple, chicken, and salad for a tasty and healthy meal that is beneficial for your medical conditions," on their smart device via visual feedback according to the user preferences, the user says, "Thank you, that helps. Let's do that." and the smart fridge manager 134 modifies the smart fridge models 132 accordingly.

The smart fridge manager 134 may facilitate one or more actions based on the one or more food consumption recommendations (step 222). As previously discussed, in embodiments, the smart fridge manager 134 may require user confirmation, approval, feedback, etc. (i.e., from step 220) in order to facilitate one or more actions. In other embodiments, the smart fridge manager 134 may simply facilitate one or more actions without requiring user confirmation. In embodiments, and with reference to FIG. 4, the smart fridge manager 134 may facilitate a scheduling of an appointment to donate food. For example, if the smart fridge manager 134 determines that a user should donate a food item at a certain time and/or day based on the user's calendar or schedule, the smart fridge manager 134 may schedule an event in the user's calendar and/or contact (i.e., via phone call, text message, email message, scheduling website, etc.) a food donation site to schedule an appointment. In embodiments, the smart fridge manager 134 may facilitate the preparation of one or more food items for consumption. For example, if a user confirms that they would like to eat an item soon for lunch, the smart fridge manager 134 may begin defrosting the item (i.e., shift item to a certain section of the smart fridge 110 with warmer temperature or eject food item outside the smart fridge 110 to a warmer temperature). In embodiments, and with reference to FIG. 5, the smart fridge manager 134 may contact one or more doctors, nurses, health professionals, etc. regarding the user's diet and/or health. For example, the smart fridge manager 134 may notify a user's doctor if the doctor asked the user to limit their sugar intake to a specified level but the user is consuming drastically more sugar than the specified level. In embodiments, the smart fridge manager 134 may facilitate one or more other actions based on the determined one or more recommendations.

With reference to the previously introduced example where the user says, "Thank you, that helps. Let's do that." and the smart fridge manager 134 modifies the smart fridge models 132 accordingly, the smart fridge manager 134 schedules an appointment with a local homeless shelter for donation of the leftover pizza on Jan. 25, 2021, and updates the user's calendar to reflect this appointment. The smart fridge manager 134 additionally begins warming the temperature of the apple, chicken, and salad in preparation for the user's consumption.

FIG. 3 depicts an exemplary flowchart illustrating the operations of a smart fridge manager 134 of the smart fridge system 100 in determining one or more preferred recipes of a user and recommending one or more recipes to the user, in accordance with the exemplary embodiments.

FIG. 4 depicts an exemplary flowchart illustrating the operations of a smart fridge manager 134 of the smart fridge system 100 in scheduling the giving away of food, in accordance with the exemplary embodiments.

FIG. 5 depicts an exemplary flowchart illustrating the operations of a smart fridge manager 134 of the smart fridge system 100 in consulting one or more doctors for feedback and making recommendations to a user based on the feedback from the one or more doctors, in accordance with the exemplary embodiments.

Figure 6:
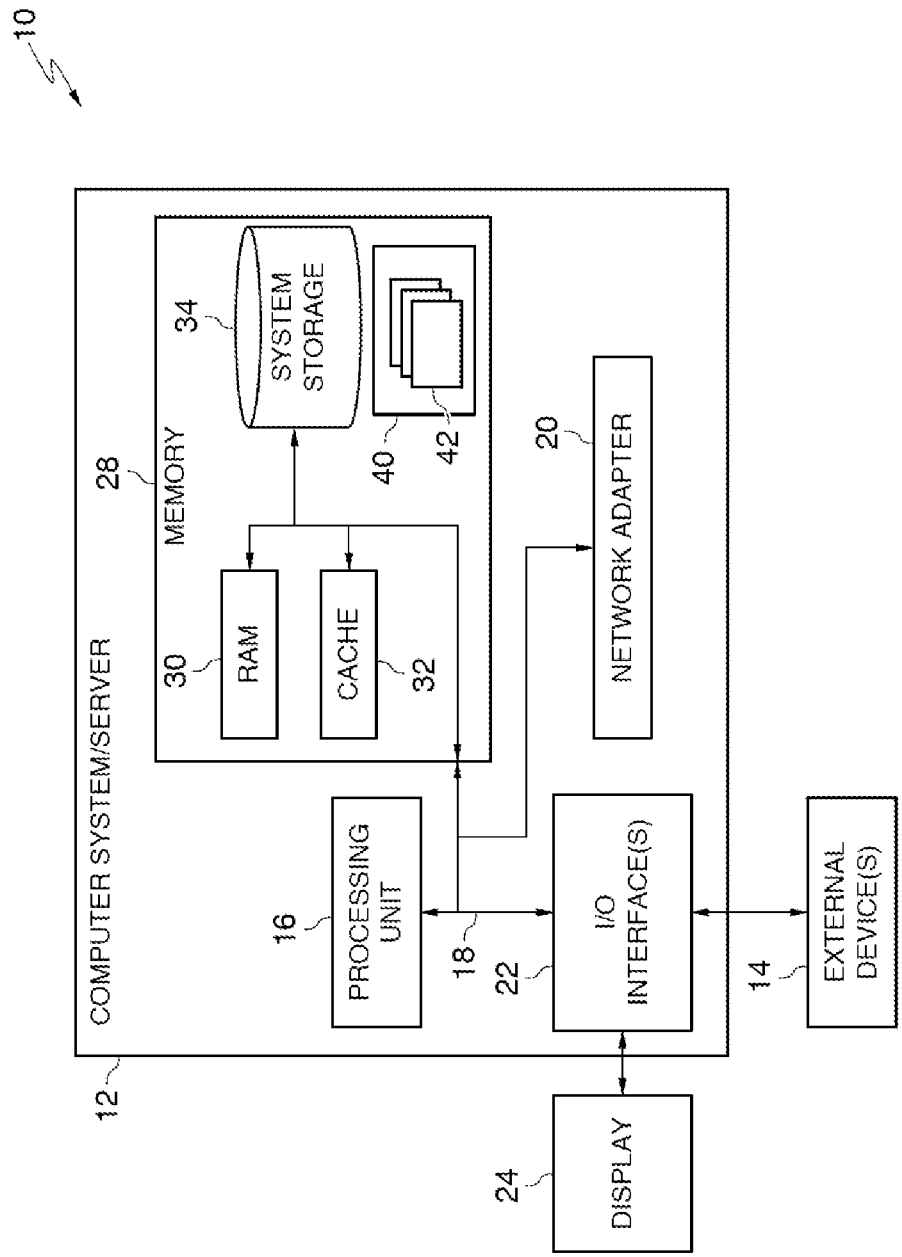
FIG. 6 depicts an exemplary block diagram depicting the hardware components of the smart fridge system 100 of FIG. 1, in accordance with the exemplary embodiments.

FIG. 6 depicts a block diagram of devices within the smart fridge system 100 of FIG. 1, in accordance with the exemplary embodiments. It should be appreciated that FIG. 6 provides only an illustration of one implementation and does not imply any limitations with regard to the environments in which different embodiments may be implemented. Many modifications to the depicted environment may be made.

Devices used herein may include one or more processors 02, one or more computer-readable RAMs 04, one or more computer-readable ROMs 06, one or more computer readable storage media 08, device drivers 12, read/write drive or interface 14, network adapter or interface 16, all interconnected over a communications fabric 18. Communications fabric 18 may be implemented with any architecture designed for passing data and/or control information between processors (such as microprocessors, communications and network processors, etc.), system memory, peripheral devices, and any other hardware components within a system.

One or more operating systems 10, and one or more application programs 11 are stored on one or more of the computer readable storage media 08 for execution by one or more of the processors 02 via one or more of the respective RAMs 04 (which typically include cache memory). In the illustrated embodiment, each of the computer readable storage media 08 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Devices used herein may also include a RAY drive or interface 14 to read from and write to one or more portable computer readable storage media 26. Application programs 11 on said devices may be stored on one or more of the portable computer readable storage media 26, read via the respective RAY drive or interface 14 and loaded into the respective computer readable storage media 08.

Devices used herein may also include a network adapter or interface 16, such as a TCP/IP adapter card or wireless communication adapter (such as a 4G wireless communication adapter using OFDMA technology). Application programs 11 on said computing devices may be downloaded to the computing device from an external computer or external storage device via a network (for example, the Internet, a local area network or other wide area network or wireless network) and network adapter or interface 16. From the network adapter or interface 16, the programs may be loaded onto computer readable storage media 08. The network may comprise copper wires, optical fibers, wireless transmission, routers, firewalls, switches, gateway computers and/or edge servers.

Devices used herein may also include a display screen 20, a keyboard or keypad 22, and a computer mouse or touchpad 24. Device drivers 12 interface to display screen 20 for imaging, to keyboard or keypad 22, to computer mouse or touchpad 24, and/or to display screen 20 for pressure sensing of alphanumeric character entry and user selections. The device drivers 12, R/W drive or interface 14 and network adapter or interface 16 may comprise hardware and software (stored on computer readable storage media 08 and/or ROM 06).

The programs described herein are identified based upon the application for which they are implemented in a specific one of the exemplary embodiments. However, it should be appreciated that any particular program nomenclature herein is used merely for convenience, and thus the exemplary embodiments should not be limited to use solely in any specific application identified and/or implied by such nomenclature.

Based on the foregoing, a computer system, method, and computer program product have been disclosed. However, numerous modifications and substitutions can be made without deviating from the scope of the exemplary embodiments. Therefore, the exemplary embodiments have been disclosed by way of example and not limitation.

It is to be understood that although this disclosure includes a detailed description on cloud computing, implementation of the teachings recited herein are not limited to a cloud computing environment. Rather, the exemplary embodiments are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or data center).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 7, illustrative cloud computing environment 50 is depicted. As shown, cloud computing environment 50 includes one or more cloud computing nodes 40 with which local computing devices used by cloud consumers, such as, for example, personal digital assistant (PDA) or cellular telephone 54A, desktop computer 54B, laptop computer 54C, and/or automobile computer system 54N may communicate. Nodes 40 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 7 are intended to be illustrative only and that computing nodes 40 and cloud computing environment 50 can communicate with any type of computerized device over any type of network and/or network addressable connection (e.g., using a web browser).

Referring now to FIG. 8, a set of functional abstraction layers provided by cloud computing environment 50 (FIG. 7) is shown. It should be understood in advance that the components, layers, and functions shown in FIG. 8 are intended to be illustrative only and the exemplary embodiments are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and food consumption recommendation 96.

The exemplary embodiments may be a system, a method, and/or a computer program product at any possible technical detail level of integration. The computer program product may include a computer readable storage medium (or media) having computer readable program instructions thereon for causing a processor to carry out aspects of the exemplary embodiments.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the exemplary embodiments may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the exemplary embodiments.

Aspects of the exemplary embodiments are described herein with reference to flowchart illustrations and/or block diagrams of methods, apparatus (systems), and computer program products according to the exemplary embodiments. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various exemplary embodiments. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method for managing a consumption of food, the method comprising:
collecting first data associated with a user;
continuously collecting second data associated with one or more food items stored inside a smart fridge using at least one sensor of the smart fridge, wherein the continuously collected second data is collectable without opening a door of the smart fridge;
extracting one or more features from the collected first data and the continuously collected second data; and
determining a food consumption recommendation in real time, based on the extracted one or more features, wherein the determined food consumption recommendation includes a donation recommendation responsive to identifying, using the at least one sensor in the smart fridge, an excess food item of the one or more food items that cannot be consumed prior to an expiration date of the excess food item; and
responsive to the determined food consumption recommendation including the donation recommendation, automatically scheduling a donation of the excess food item with a third-party prior to the expiration date of the excess food item.

2. The method of claim 1, wherein the determined food consumption recommendation further comprises a recipe recommendation and a medical recommendation, and wherein the method further comprises generating a notification for comprising: notifying the user of the determined food consumption recommendation.

3. The method of claim 2, further comprising:
receiving a confirmation of the determined food consumption recommendation from the user;
adjusting the one or more models based on the received confirmation; and
facilitating one or more actions based on the determined food consumption recommendation.

4. The method of claim 3, wherein the one or more actions are selected from the group consisting of: scheduling a time to donate food, defrosting one or more of the food items, and notifying one or more medical professionals.

5. The method of claim 1, wherein the one or more models correlate the one or more features with the likelihood of determining an appropriate food consumption recommendation.

6. The method of claim 1, further comprising:
collecting training data;
extracting training features from the training data; and
training the one or more models based on the extracted training features.

7. The method of claim 1, wherein the one or more features are selected from the group consisting of: item types, dates purchased of items, expiration dates of items, shelf lives of items, quantities of items, temperatures of items, humidity of items, possible recipes of items, recipe preparation times of items, healthiness of items, user calendars, user schedules, user medical information, user allergy information, user dietary restrictions, and user dietary preferences.

8. A computer program product for managing a consumption of food, the computer program product comprising: one or more non-transitory computer-readable storage media and program instructions stored on the one or more non-transitory computer-readable storage media capable of performing a method, the method comprising:
collecting first data associated with a user;
continuously collecting second data associated with one or more food items stored inside a smart fridge using at least one sensor of the smart fridge, wherein the continuously collected second data is collectable without opening a door of the smart fridge;
extracting one or more features from the collected first data and the continuously collected second data; and
determining a food consumption recommendation in real time, based on the extracted one or more features, wherein the determined food consumption recommendation includes a donation recommendation responsive to identifying, using the at least one sensor in the smart fridge, an excess food item of the one or more food items that cannot be consumed prior to an expiration date of the excess food item; and
responsive to the determined food consumption recommendation including the donation recommendation, automatically scheduling a donation of the excess food item with a third-party prior to the expiration date of the excess food item.

9. The computer program product of claim 8, wherein the determined food consumption recommendation further comprises a recipe recommendation and a medical recommendation, and wherein the method further comprises generating a notification for the user of the determined food consumption recommendation.

10. The computer program product of claim 9, further comprising:
receiving a confirmation of the determined food consumption recommendation from the user;
adjusting the one or more models based on the received confirmation; and
facilitating one or more actions based on the determined food consumption recommendation.

11. The computer program product of claim 10, wherein the one or more actions are selected from the group consisting of: scheduling a time to donate food, defrosting one or more of the food items, and notifying one or more medical professionals.

12. The computer program product of claim 8, wherein the one or more models correlate the one or more features with the likelihood of determining an appropriate food consumption recommendation.

13. The computer program product of claim 8, further comprising:
collecting training data;
extracting training features from the training data; and
training the one or more models based on the extracted training features.

14. The computer program product of claim 8, wherein the one or more features are selected from the group consisting of: item types, dates purchased of items, expiration dates of items, shelf lives of items, quantities of items, temperatures of items, humidity of items, possible recipes of items, recipe preparation times of items, healthiness of items, user calendars, user schedules, user medical information, user allergy information, user dietary restrictions, and user dietary preferences.

15. A computer system for managing a consumption of food, the computer system comprising:

one or more computer processors, one or more computer-readable storage media, and program instructions stored on the one or more of the computer-readable storage media for execution by at least one of the one or more processors capable of performing a method, the method comprising:

collecting first data associated with a user;

continuously collecting second data associated with one or more food items stored inside a smart fridge using at least one sensor of the smart fridge, wherein the continuously collected second data is collectable without opening a door of the smart fridge;

extracting one or more features from the collected first data and the continuously collected second data; and determining a food consumption recommendation in real time, based on the extracted one or more features, wherein the determined food consumption recommendation includes a donation recommendation responsive to identifying, using the at least one sensor in the smart fridge, an excess food item of the one or more food items that cannot be consumed prior to an expiration date of the excess food item; and responsive to the determined food consumption recommendation including the donation recommendation, automatically scheduling a donation of the excess food item with a third-party prior to the expiration date of the excess food item.

16. The computer system of claim 15, wherein the determined food consumption recommendation further comprises a recipe recommendation and a medical recommendation, and wherein the method further comprises generating a notification for the user of the determined food consumption recommendation.

17. The computer system of claim 16, further comprising:
receiving a confirmation of the determined food consumption recommendation from the user;
adjusting the one or more models based on the received confirmation; and
facilitating one or more actions based on the food consumption recommendation.

18. The computer system of claim 17, wherein the one or more actions are selected from the group consisting of: scheduling a time to donate food, defrosting one or more of the food items, and notifying one or more medical professionals.

19. The computer system of claim 15, wherein the one or more models correlate the one or more features with the likelihood of determining an appropriate food consumption recommendation.

20. The computer system of claim 15, further comprising:
collecting training data;
extracting training features from the training data; and
training the one or more models based on the extracted training features.

* * * * *